United States Patent [19]

Conforti

[11] 4,225,860
[45] Sep. 30, 1980

[54] SENSITIVITY CONTROLLED DUAL INPUT FIRE DETECTOR

[75] Inventor: Frederick J. Conforti, Aurora, Ill.

[73] Assignee: Pittway Corporation, Northbrook, Ill.

[21] Appl. No.: 3,728

[22] Filed: Jan. 15, 1979

[51] Int. Cl.³ .............................................. G08B 17/10
[52] U.S. Cl. .................................. 340/629; 250/381; 250/574; 340/517; 340/630
[58] Field of Search ............... 340/628, 629, 630, 517, 340/521, 522; 250/381, 574

[56] References Cited

U.S. PATENT DOCUMENTS

| 3,611,335 | 10/1971 | Ogden et al. | 340/629 X |
| 3,895,367 | 7/1975 | Visser | 340/629 X |
| 4,090,177 | 5/1978 | Urata et al. | 340/630 |

FOREIGN PATENT DOCUMENTS 2452839  5/1975  Fed. Rep. of Germany ........... 340/521
2307319
Ad.76104-71  5/1976  France ............................... 340/517

Primary Examiner—John W. Caldwell, Sr.
Assistant Examiner—Daniel Myer
Attorney, Agent, or Firm—Gary, Juettner & Pyle

[57] ABSTRACT

An improved fire detector has both ionization chamber and photoelectric type products of combustion sensing devices, both of which must detect combustion for an alarm to be generated. The sensing devices are each adjusted to a quiescent sensitivity, but upon combustion being detected by one of the devices the sensitivity of the other device is automatically increased. In this manner, the detector operates very reliably to generate an alarm in the very early stages of a fire irrespective of whether the combustion process generates primarily visible or generally invisible type products of combustion, yet spurious generation of false alarm is minimized.

14 Claims, 1 Drawing Figure

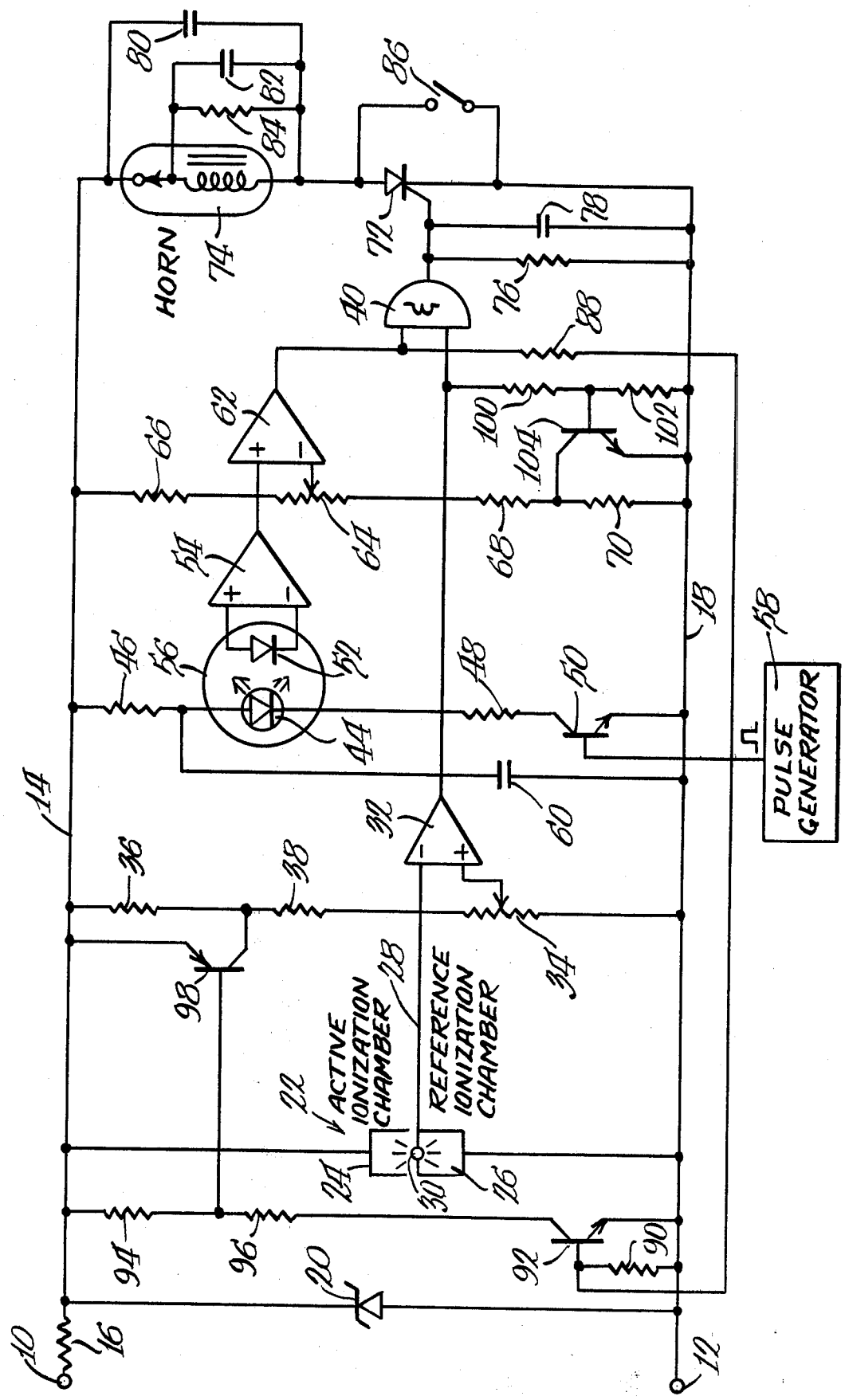

SENSITIVITY CONTROLLED DUAL INPUT FIRE DETECTOR

BACKGROUND OF THE INVENTION

The present invention relates to warning devices, and in particular to an improved fire detector which is highly responsive to the occurrence of various types of combustion, yet in which the spurious occurrence of false alarms is minimized.

Fire detectors have heretofore been primarily of two basic types, i.e., those which use an ionization chamber type sensing device to detect combustion, and those using a photoelectric sensing device. Although each type provides good relability for certain types of fires, neither by itself offers optimal protection against all of the various types of fires that might be encountered.

Ionization chamber type fire detectors, for example, are quite sensitive to the generally invisible constituents of products of combustion, for example those generated in the early stages of spontaneous combustion or by an open fire. However, such detectors are less sensitive to the visible constituents of products of combustion, such as smoke, as would be generated by a smouldering fire. Also, this type of detector is somewhat susceptible to the spurious generation of false alarms upon the occurrence of various atmospheric conditions which might normally be encountered in a residential structure, for example from products discharged into the air by cooking foods or a breeze which blows charged ions out of the ionization chamber.

Photoelectric type fire detectors, on the other hand, are quite sensitive to visible products of combustion, but not to the invisible products. In addition, these detectors are also susceptible to certain atmospheric conditions to generate a false alarm, for example atmospheric dust or smoke from a cigarette.

In an attempt to obtain the advantages of both of the aforementioned types of fire detectors in a single unit, some detectors are now available which use both ionization chamber and photoelectric types of sensing devices. In operation of such detectors, the sensing devices are each adjusted to a predetermined sensitivity, and an alarm is generated when either indicates that combustion has occurred. Although such detectors reliably detect both visible and invisible products of combustion, their response to naturally occurring atmospheric conditions is less than satisfactory and they are very prone to generate false alarms. This may be appreciated if it is considered that each of the ionization chamber and photoelectric sensing devices is sensitive to its own unique types of naturally occurring atmospheric disturbances to indicate combustion, so that a combination of both sensing devices in a single detector results in a sensitivity of the detector to significant numbers of natural atmospheric phenomena.

OBJECTS OF THE INVENTION

An object of the present invention is to provide a fire detector having both ionization chamber and photoelectric type sensing devices, which is very sensitive to the occurrence of combustion to generate an alarm and yet which minimizes the spurious occurrence of false alarms.

Another object of the invention is to provide such a fire detector in which both sensing devices must detect combustion for an alarm to be generated, but in which detection of combustion by one of the devices automatically increases the sensitivity of the other device.

SUMMARY OF THE INVENTION

In accordance with the present invention, a warning device for detecting the occurrence of predetermined phenomena comprises first detector means responsive to the phenomena for generating a first signal upon the occurrence thereof and second detector means responsive to the phenomena for generating a second signal upon the occurrence thereof, said first and second detector means having selected sensitivities to predetermined minimum concentrations of the phenomena to generate said first and second signals. Also included are means for changing the sensitivity of said first detector means to the phenomena upon generation of said second signal, means for changing the sensitivity of said second detector means to the phenomena upon generation of said first signal, and means for indicating the simultaneous generation of said first and second signals.

Preferably, the warning device is a fire detector for detecting the occurrence of products of combustion, said first detector means includes an ionization chamber products of combustion detecting device for generating a signal having a value in accordance with concentrations of products of combustion and first means for monitoring the value of said signal and for generating at an output therefrom said first signal upon said ionization chamber signal having a selected value, and said second detector means included a photoelectric products of combustion sensing device for generating a signal having a value in accordance with concentrations of products of combustion and second means for monitoring the value of said photoelectric device signal and for generating at an output therefrom said second signal upon said photoelectric device signal having a selected value. Circuit means couples said first monitoring means output with said second monitoring means for controlling the response of said second monitoring means to the value of said photoelectric device signal, and couples said second monitoring means output with said first monitoring means to control the response to said first monitoring means to the value of said ionization chamber signal, so that said first monitoring means generates said first signal when said ionization chamber signal has a first value in the absence of said second signal and a second value upon occurrence of said second signal, and so that said second monitoring means generates said second signal when said photoelectric device signal has a third value in the absence of said first signal and a fourth value upon occurrence of said first signal.

To accomplish the foregoing, means are provided for generating a first reference signal, and said first monitoring means compares the values of said ionization chamber device signal and said first reference signal and generates said first signal when said ionization chamber signal has a selected value with respect to said reference signal. Means are also provided for generating a second reference signal, and said second monitoring means compares the values of said photoelectric device signal and said second reference signal and generates said second signal when said photoelectric device signal has a selected value with respect to said reference signal. Said circuit means for coupling said first and second monitoring means includes means connected with said first and second reference signal generating means for changing said first reference signal from a first to a second value upon occurrence of said second signal and for changing said second reference signal from a third to a fourth value upon occurrence of said first signal. The arrangement is such that when neither said first or said second signal is being generated, predetermined minimum concentrations of products of combustion must be sensed by said ionization chamber device or by said photoelectric device for one of said signals to be generated, but upon one of said signals being generated then lesser predetermined concentrations of products of combustion are required to be sensed by said other device for said other signal to be generated.

The fire detector of the invention thus responds very rapidly to the occurrence of combustion irrespective of whether the products generated thereby are primarily of a generally invisible type to which the ionization chamber device is particularly sensitive or of a visible type to which the photoelectric device is particularly sensitive. At the same time, the fire detector is not prone to the spurious generation of false alarms, since not only must both of the ionization chamber and photoelectric devices respond for an alarm to be generated, but also their sensitivities may be set at an initial value which makes the devices relatively immune to atmospheric disturbances of a noncombustion nature, yet which enables both of the devices to rapidly respond should combustion occur.

The foregoing and other objects, advantages and features of the invention will become apparent upon a consideration of the following detailed description, when taken in conjunction with the accompanying drawings.

BRIEF DESCRIPTION OF THE DRAWINGS

The single drawing FIGURE is a schematic circuit representation of a fire detector constructed in accordance with a preferred embodiment of the invention.

DETAILED DESCRIPTION

Referring to the drawing, there is shown in accordance with the teachings of the present invention a warning device having first and second detector means, each of which is primarily responsive to separate constituent parts of a phenomena to be detected, and which for the embodiment of the invention illustrated and described comprises a fire detector having both ionization chamber and photoelectric type products of combustion sensing devices. The sensing devices are adjusted to an initial sensitivity to products of combustion, and both must indicate the occurrence of combustion in order for an alarm to be generated. In accordance with the present invention, however, upon one of the devices sensing combustion, the sensitivity of the other device to products of combustion is increased, whereby the first detector is highly responsive to the occurrence of combustion irrespective of the nature of the products thereof, and the generation of false or spurious alarms is minimized.

More specifically, the fire detectors includes a pair of input terminals 10 and 12, with the input terminal 10 being connected with a conductor 14 through a resistor 16 and the input terminal 12 being connected to a conductor 18. The terminals are connectable with a suitable source of d.c. voltage, for example a rectified a.c. voltage or a battery, and with the terminal 10 at a positive potential with respect to the terminal 12 means, such as a zener diode 20, preferably is provided to regulate the voltage across the conductors to a predetermined value.

The ionization chamber type sensing device is indicated generally at 22, and includes an active ionization chamber 24 connected in series with a reference ionization chamber 26 between the conductors 14 and 18. A common electrode 28 is positioned between and separates the chambers, and a source of radiation, for example americium 241, ionizes air molecules within the chambers. In this manner, a current flows through the chambers and generates at the electrode a voltage having a value in accordance with the relative impedance of the chambers.

The active chamber 24 is relatively open to atmosphere and the reference chamber 26 is relatively closed, so that upon the occurrence of combustion products of combustion concentrate in the active chamber more rapidly than in the reference chamber, the impedance of the active chamber increases with respect to that of the reference chamber, and the voltage at the electrode 28 decreases to indicate detection of combustion. For naturally occurring slow changes in atmospheric conditions, however, such as changes in temperature, relative humidity and barometric pressure which affect the impedances of the chambers, the impedance of the reference chamber changes simultaneously with and in proportion to the impedance of the active chamber, and the voltage at the electrode 28 remains substantially constant.

To detect changes in the voltage at the electrode 28 which are representative of combustion, an operational amplifier (op amp) 32 is connected at its inverting input with the electrode and at its noninverting input with the slider of a potentiometer 34 in series with a pair of resistors 36 and 38 between the conductors 14 and 18. To adjust the sensitivity of the ionization chamber portion of the fire detector to products of combustion, under quiescent conditions and in the absence of products of combustion the slider of the potentiometer is set so that the voltage at the noninverting input to the op amp is negative with respect to that at the inverting input by a predetermined amount, which is equal to the amount of change in voltage that must occur at the electrode in response to predetermined concentrations of products of combustion in the active chamber for the inverting input to become negative with respect to the noninverting input to provide an output from the op amp. For the purpose of reference, when the voltage at the inverting input to the op amp is positive with respect to that at the noninverting input, the output from the op amp is considered to be at a "0" state, and when the voltage at the inverting input is negative with respect to that at the noninverting input the output is considered to be at a "1" state. Thus, in the absence of combustion the op amp output is 0, but upon the occurrence of products of combustion in sufficient concentrations the output changes to 1. The output from the op amp is connected with a first input to an AND gate 40.

The ionization chamber assembly is highly responsive to the generally invisible components or constituents of products of combustion, for example those generated in the early stages of spontaneous combustion or by open fire. The chamber assembly is less responsive, however, to the visible constituents of products of combustion, such as those emitted by a smouldering fire, and for this reason the fire detector also includes a photoelectric type products of combustion sensing device. The photoelectric sensing device is more responsive to visible constituents of products of combustion than is the ionization chamber device, but is not nearly as responsive to the invisible constituents, whereby the two devices complement each other and enable the fire detector to respond very rapidly to combustion irrespective of whether the products generated thereby are primarily visible or invisible, as will be described.

The photoelectric detecting device is indicated generally at 42, and includes a light emitting diode (LED) 44 connected in series with a pair of resistors 46 and 48 and an NPN transistor 50 between the conductors 14 and 18, and a light receiving diode or photodetector 52 connected at its anode with the noninverting input to an op amp 54 and at its cathode with the inverting input. The LED and the photodetector are contained within a housing 56 which is relatively open to atmosphere but closed to external light. The housing is internally configured so that there is no direct path for light from the LED to the photodetector, but so that upon the occurrence of visible particles within the housing light from the LED is reflected off of the particles and onto the photodetector.

In operation of the photoelectric sensing device, and to conserve energy where the power source is a battery, a pulse generator 58 is connected to the base of the transistor 50 for intermittently rendering the same conductive to illuminate the LED 44. To this end, and to provide sufficient current to properly illuminate the LED, a capacitor 60 is connected between the anode of the LED and the conductor 18 for being charged through the resistor 46 when the transistor is nonconductive, and for being discharged through the LED when the transistor conducts. In the absence of visible particles within the housing 56, upon illumination of the LED no light strikes the photodetector 52 and the output from the op amp 54 remains constant. Upon the presence of visible particles within the housing, however, upon illumination of the LED light is reflected off of the particles and onto the photodetector to change the conductive state thereof in accordance with the concentrations of the particles, and the output from the op amp changes accordingly.

The output from the op amp 54 is applied to a noninverting input to an op amp 62, the inverting input to which is connected with the slider of a potentiometer 64 in series with three resistors 66, 68 and 70 between the conductors 14 and 18. To adjust the sensitivity of the photoelectric device 42 to products of combustion, under quiescent conditions and in the absence of visible particles within the housing 56 the slider of the potentiometer is set so that the voltage at the inverting input to the op amp 62 is positive with respect to the voltage at the noninverting input by a predetermined amount, that being the amount of change required in the output voltage of the op amp 54 to cause the output from the op amp 62 to change from a 0 to a 1 state. The output from the op amp 62 is connected to a second input to the AND gate 40.

Upon the simultaneous occurrence of 1 states at each of the outputs from the op amps 32 and 62 in response to both of the ionization chamber and photoelectric devices detecting combustion, the AND gate provides a 1 input to the gate of an SCR 72 to trigger the SCR and energize an alarm, such as a horn 74 connected in series with the SCR between the conductors 14 and 18. A resistor 76 and a capacitor 78 connected in parallel between the output from the AND gate and the conductor 18 minimize spurious triggering of the SCR, and a pair of capacitors 80 and 82 and a resistor 84 provides noise suppression for the horn. The alarm is then sounded until the 1 signal is removed from the gate of the SCR, whereupon the SCR becomes nonconductive to silence the horn upon the next opening of the horn contacts. If desired, to test operation of the horn in the absence of combustion a manually manipulatable switch 86 may be connected across the anode and the cathode of the SCR.

Although the fire detector thus far described would reliably generate an alarm upon the occurrence of certain types of combustion, for example those characterized by the simultaneous production of sufficient concentrations of both visible and invisible products of combustion, it would not satisfactorily respond to all types of fires. For instance, upon the occurrence of combustion characterized primarily by the production of the invisible constituents of products of combustion an output would quickly be generated by the ionization chamber device, but not by the photoelectric device, and therefore a warning of combustion would not be given at the earliest possible stage of the fire. On the other hand, should the fire be characterized primarily by the production of the visible constituents of products of combustion, then although the photoelectric device would rapidly detect the combustion, the ionization chamber device would not.

Prior attempts to overcome the aforementioned disadvantages of dual sensing device fire detectors have included significantly increasing the sensitivities of the sensing devices to products of combustion, the thought being that even if a fire generated products of combustion which were primarily either visible or invisible, due to their increased sensitivities the devices would nevertheless respond at an early stage of combustion. Although increasing the sensitivities did result in a faster response to all types of combustion, in use of the detectors it was found that naturally occurring atmospheric conditions, which otherwise would not have been sufficient to affect the outputs of less sensitive detecting devices, caused an unacceptably high incidence of false alarms to be generated.

Another prior attempt contemplated generating an alarm upon only one of the devices detecting combustion. This, however, was also unacceptable from the standpoint of false alarms, since the sensing devices were then individually responsive to noncombustion type atmospheric disturbances to trigger the detector.

The present invention overcomes the aforementioned disadvantages of the prior art by providing means for controlling the sensitivities to combustion of both the ionization chamber and photoelectric sensing devices in a manner which optimizes their response to combustion, and yet minimizes the occurrence of false alarms. In particular, the sensitivities are controlled so that the devices have a selected sensitivity under quiescent conditions in the absence of products of combustion, but upon one of the devices detecting combustion the sensitivity of the other device is increased.

To accomplish the foregoing, and with the sensitivity of the ionization chamber assembly 22 adjusted to an initial quiescent value by means of the potentiometer 34, means for increasing its sensitivity upon detection of combustion by the photoelectric device 42 includes a pair of resistors 88 and 90 connected in series between the output from the op amp 62 and the conductor 18. The base of an NPN transistor 92 is connected to the juncture between the resistors, the collector-emitter circuit of the transistor is in series with a pair of resistors 94 and 96 between the conductors 14 and 18, and a PNP transistor 98 is connected at its base with the juncture between the resistors 94 and 96 and with its collector-emitter circuit across the resistor 36.

The arrangement is such that when the output from the op amp 62 is at a 0 state, the transistors 92 and 98 are nonconductive and the sensitivity of the ionization chamber assembly is determined by the values of the resistors 36 and 38 and by the setting of the potentiometer 34. Upon detection of products of combustion by the photoelectric device, however, the output from the op amp 62 changes to a 1 state and renders the transistors 92 and 98 conductive. Conduction of the transistor 98 shorts the resistor 36 out of circuit with the resistor 38 and the potentiometer 34, and increases the voltage at the noninverting input to the op amp 32. Under this condition, the voltage at the electrode 28 of the ionization chamber assembly then has to change or decrease by a lesser predetermined amount for the inverting input to the op amp to become negative with respect to the noninverting input in order to provide a 1 state at the output from the op amp, whereby the sensitivity of the ionization chamber assembly is increased. It is understood, of course, that the value of the resistor 36 may be selected to increase the sensitivity of the ionization chamber assembly by any desired amount, provided that its removal in the absence of products of combustion does not by itself cause the op amp to generate a 1 state output indicative of combustion. Thus, upon detection of products of combustion by the photoelectric sensing device 42, smaller concentrations of products of combustion are thereafter required to occur in the active chamber 24 in order to alarm the fire detector.

In a somewhat similar manner, detection of products of combustion by the ionization chamber assembly automatically increases the sensitivity of the photoelectric sensing device to visible products of combustion. To this end, a pair of resistors 100 and 102 are in series between the output from the op amp 32 and the conductor 18, and an NPN transistor 104 is connected at its base with the juncture between the resistors 100 and 102 and with its collector-emitter circuit across the resistor 70. With the sensitivity of the photoelectric sensing device adjusted to an initial or quiescent value in the absence of products of combustion by means of the resistors 66, 68 and 70 and the setting of the potentiometer 64, upon detection of combustion by the ionization chamber assembly the 1 signal generated at the output from the op amp 32 turns on the normally nonconductive transistor 104 to shunt across or short out the resistor 70. This decreases the voltage at the inverting input to the op amp 62 by a predetermined amount, whereby the voltage at the noninverting input is required to change or increase by a lesser predetermined amount for a 1 signal to be generated by the op amp. Thus, upon detection of products of combustion by the ionization chamber assembly, the sensitivity of the photoelectric sensing device is increased, whereby lesser concentrations of visible products of combustion are required to occur in the housing 56 for a 1 state to be generated at the output from the op amp 62 to initiate an alarm. The value of the resistor 70 may, of course, be selected to increase the sensitivity of the photoelectric sensing device by any desired amount, provided that its removal in the absence of products of combustion does not by itself cause the op amp 62 to generate a 1 state output indicative of combustion.

The invention thus provides an improved warning device which is highly responsive to all types of combustion to generate an alarm. Should the products of combustion be primarily of the invisible type to which the ionization chamber 22, but not the photoelectric sensing device 42, is particularly responsive, then upon a 1 state occurring at the output from the op amp 32 the sensitivity of the photoelectric device is increased, whereby lower concentrations of visible products of combustion are required to occur within the housing 56 to cause generation of an alarm. Similarly, should the products of combustion be primarily of the visible type to which the photoelectric device, but not the ionization chamber, is particularly sensitive, then upon occurrence of a 1 state at the output from the op amp 62 the sensitivity of the ionization chamber assembly is increased, whereby lesser concentrations of the generally invisible products of combustion are required to occur in the active ionization chamber 24 in order to generate an alarm.

It is also to be appreciated that the unique operation of the fire detector also results in the same being relatively insensitive to natural occurring atmospheric disturbances which might otherwise cause a false alarm to be generated by a detector of a type including only one of the sensing devices. In particularly, in the initial stages of combustion concentrations of visible and/or generally invisible products of combustion increase rapidly, so that at least one of the sensing devices, even when set to a relatively low "false alarm" safe sensitivity, will rapidly detect the occurrence of combustion and increase the sensitivity of the other sensing device. Thus, in order to provide highly reliable fire detection the sensitivities of the devices need not be adjusted to high values under quiescent conditions, so that the sensitivities of the devices to atmospheric disturbances are decreased. Consequently, the fire detector responds only to the occurrence of combustion to generate an alarm, and not to other noncombustion atmospheric disturbances.

While one particular embodiment of the invention has been described in detail, it is understood that various modifications and other embodiments thereof may be devised by one skilled in the art without departing from the spirit and scope of the invention, as defined by the appended claims.

What is claimed is:

1. A warning device for detecting the occurrence of predetermined phenomena, comprising first detector means responsive to the phenomena for generating a first signal upon the occurrence thereof; second detector means responsive to the phenomena for generating a second signal upon the occurrence thereof, said first and second detector means having selected discrete sensitivities to predetermined concentrations of the phenomena to generate said first and second signals; means for changing the sensitivity of said first detector means to the phenomena from a first to a second discrete value upon generation of said second signal; means for changing the sensitivity of said second detector means to the phenomena from a third to a fourth discrete value upon generation of said first signal; and means for indicating the simultaneous generation of said first and second signal.

2. A warning device as in claim 1, said means for changing the sensitivities of said first and said second detector means increasing the sensitivities thereof.

3. A warning device as in claim 1, the predetermined phenomena being products of combustion, said first detector means including ionization chamber products of combustion sensing means, and said second detector means including photoelectric products of combustion sensing means.

4. A warning device as in claim 1, said first detector means including first sensing means for generating a signal having a value in accordance with concentrations of the phenomena and first means for monitoring said first sensing means signal and for generating said first signal when said first sensing means signal has a selected value; said second detector means including second sensing means for generating a signal having a value in accordance with concentrations of the phenomena, and second means for monitoring said second sensing means signal and for generating said second signal when said second sensing means signal has a selected value; said means for changing the sensitivity of said first detector means including first circuit means connected between said first monitoring means and said second monitoring means for controlling operation of said first monitoring means so that the same generates said first signal when said first sensing means signal has a first discrete value in the absence of, or a second discrete value upon generation of, said second signal; said means for changing the sensitivity of said second detector means including second circuit means connected between said second monitoring means and said first monitoring means for controlling operation of said second monitoring means so that the same generates said second signal when said second sensing means signal has a third discrete value in the absence of, or a fourth discrete value upon generation of, said first signal.

5. A warning device as in claim 1, said first detector means including first sensing means for generating a voltage signal having a value in accordance with concentrations of the phenomena, means for generating a first reference potential, and means for comparing the values of said voltage signal and said reference potential and for generating said first signal when a predetermined difference in value exists between the same; said second detector means including second sensing means for generating a voltage signal having a value in accordance with concentrations of the phenomena, means for generating a second reference potential, and means for comparing the values of said second sensing means voltage signal and said second reference potential and for generating said second signal when a predetermined difference in value exists between the same; said means for changing the sensitivity of said first detector means including means for changing said first reference potential from a first to a second discrete value upon generation of said second signal; said means for changing the sensitivity of said second detector means including means for changing said second reference potential from a third to a fourth discrete value upon generation of said first signal.

6. A warning device as in claim 1, wherein the predetermined phenomena comprises concentrations of at least two constituents, said first detector means being more responsive to predetermined concentrations of one of the constituents than to the others to generate said first signal, said second detector means being more responsive to predetermined concentrations of another of the constituents than to the others to generate said second signal.

7. A warning device for detecting the occurrence of predetermined phenomena having concentrations of at least first and second constituents, comprising first detector means responsive to the occurrence of the phenomena to generate a first signal, said first detector means being more responsive to the occurrence of predetermined concentrations of the first constituent than of the second constituent to generate said first signal; second detector means response to the occurrence of the phenomena to generate a second signal, said second detector means being more responsive to the occurrence of predetermined concentrations of the second constituent than of the first constituent to generate said second signal, said first and second detector means having selected discrete sensitivities to predetermined concentrations of the first and second constituents, respectively, to generate said first and second signals; means for increasing the sensitivity of said first detector means to the first constituent from a first to a second discrete value upon generation of said second signal; means for increasing the sensitivity of said second detector means to the second constituent from a third to a fourth discrete value upon generation of said first signal; and means for indicating the simultaneous generation of said first and second signals.

8. A warning device as in claim 7, wherein the predetermined phenomena are products of combustion, the first constituent is visible products of combustion, the second constituent is generally invisible products of combustion, said first detector means includes photoelectric products of combustion sensing means, and said second detector means includes ionization chamber products of combustion sensing means.

9. A fire detector for detecting the occurrence of products of combustion, comprising first detector means including an ionization chamber sensing device for generating a first signal upon the occurrence of products of combustion; second detector means including a photoelectric sensing device for generating a second signal upon the occurrence of products of combustion, said first and second detector means having selected discrete sensitivities to predetermined concentrations of products of combustion to generate said first and said second signals; means for increasing the sensitivity of said first detector means to products of combustion from a first to a second discrete value upon said second signal being generated, whereby said first detector means generates said first signal in response to lower concentrations of products of combustion than when said second signal is not being generated; means for increasing the sensitivity of said second detector means to products of combustion from a third to a fourth discrete value upon said first signal being generated, whereby said second detector means generates said second signal in response to lower concentrations of products of combustion than when said first signal is not being generated; and means for indicating the simultaneous generation of said first and second signals.

10. A fire detector as in claim 9, said ionization chamber sensing device generating an output signal having a value in accordance with concentrations of products of combustion and said first detector means including first means for monitoring the value of said output signal and for generating said first signal, said first monitoring means being coupled with said second detector means and generating said first signal when said ionization chamber device output signal has a first discrete value in the absence of, and a second discrete value upon generation of, said second signal; said photoelectric sensing device generating an output signal having a value in accordance with concentrations of products of combustion and said second detector means including second means for monitoring the value of said photoelectric device output signal and for generating said second signal, said second monitoring means being coupled with said first detector means and generating said second signal when said photoelectric sensing device output signal has a third discrete value in the absence of, and a fourth discrete value upon generation of, said first signal.

11. A fire detector as in claim 10, including means for generating a first reference signal, said first monitoring means comparing the values of said ionization chamber device output signal and said first reference signal and generating said first signal when a predetermined difference in value exists between the same; and means for generating a second reference signal, said second monitoring means comparing the values of said photoelectric device output signal and said second reference signal and generating said second signal when a predetermined difference in value exists between the same; said means for increasing the sensitivity of said first detector means including first circuit means coupled between said second monitoring means and said means for generating said first reference signal for changing said first reference signal from a first to a second discrete value upon generation of said second signal; said means for increasing the sensitivity of said second detector means including second circuit means coupled between said first monitoring means and said means for generating said second reference signal for changing said second reference signal from a third to a fourth discrete value upon generation of said first signal.

12. A fire detector for detecting the presence of products of combustion, comprising first sensor means including an ionization chamber for generating a first signal upon the occurrence of products of combustion; second sensor means including a photoelectric device for generating a second signal upon the occurrence of products of combustion; first circuit means coupled with said first and second sensor means for controlling said first sensor means so that the same generates said first signal in response to at least first discrete concentrations of products of combustion in the absence of said second signal and in response to at least second and lesser discrete concentrations of products of combustion upon generation of said second signal; second circuit means coupled with said first and second sensor means for controlling said second sensor means so that the same generates said second signal in response to at least third discrete concentrations of products of combustion in the absence of said first signal and in response to at least fourth and lesser discrete concentrations of products of combustion upon generation of said first signal; and means for indicating the simultaneous generation of said first and second signals.

13. A method of detecting the occurrence of predetermined phenomena, comprising the steps of sensing the phenomena with a first detector and generating a first signal upon the occurrence thereof, sensing the phenomena with a second detector and generating a second signal upon the occurrence thereof; changing the sensitivity of the first detector from a first to a second discrete value upon generation of the second signal; changing the sensitivity of the second detector from a third to a fourth discrete value upon generation of the first signal; and indicating the simultaneous generation of the first and second signals.

14. A method of detecting the occurrence of predetermined phenomena having concentrations of at least first and second constituents, comprising the steps of sensing the phenomena with a first detector and generating a first signal upon occurrence thereof, wherein the first detector is more responsive to predetermined concentrations of the first constituent than of the second constituent to generate the first signal; sensing the phenomena with a second detector and generating a second signal upon occurrence thereof, wherein the second detector is more responsive to predetermined concentrations of the second constituent than of the first constituent to generate the second signal; increasing the sensitivity of the first detector to the first constituent from a first to a second discrete value upon generation of the second signal; increasing the sensitivity of the second detector to the second constituent from a third to a fourth discrete value upon generation of the second signal; and indicating the simultaneous occurrence of the first and second signals.

* * * * *